United States Patent [19]

Neuber et al.

[11] Patent Number: 5,396,012
[45] Date of Patent: Mar. 7, 1995

[54] PROCESS FOR THE PREPARATION OF MONOISOPROPYLNAPHTHALENE

[75] Inventors: Marita Neuber, Frankfurt am Main; Udo Dettmeier, Kelkheim; Ernst I. Leupold, Neu-Anspach, all of Germany

[73] Assignee: Hoechst Aktiengesellschaft, Frankfurt am Main, Germany

[21] Appl. No.: 980,988

[22] Filed: Nov. 24, 1992

[30] Foreign Application Priority Data

Nov. 30, 1991 [DE] Germany .......................... 4139548.4

[51] Int. Cl.6 .............................................. C07C 2/68
[52] U.S. Cl. .................................................. 585/467
[58] Field of Search ........................................ 585/467

[56] References Cited

U.S. PATENT DOCUMENTS

| | | | |
|---|---|---|---|
| 3,236,762 | 2/1966 | Rabo et al. | 585/467 |
| 3,251,897 | 5/1966 | Wise . | |
| 3,631,120 | 12/1971 | Eberly, Jr. . | |
| 3,851,004 | 11/1974 | Yang | 585/467 |
| 4,112,008 | 9/1978 | Marcilly | 585/467 |
| 4,570,027 | 2/1986 | Boucher et al. | 585/467 |

FOREIGN PATENT DOCUMENTS

| | | |
|---|---|---|
| 1043816 | 12/1978 | Canada . |
| 338292 | 10/1989 | European Pat. Off. . |
| 432132 | 6/1991 | European Pat. Off. . |
| 1468982 | 8/1973 | Germany . |
| WO92/07810 | 5/1992 | WIPO . |

*Primary Examiner*—Helen M. S. Sneed
*Assistant Examiner*—E. D. Irzinski

[57] ABSTRACT

Process for the preparation of monoisopropylnaphthalene by alkylation of naphthalene with the aid of zeolites of the faujasite type as catalysts, wherein the cations of the zeolites have been replaced by alkaline earth metal ions.

16 Claims, No Drawings

PROCESS FOR THE PREPARATION OF MONOISOPROPYLNAPHTHALENE

The present invention relates to a process for the preparation of monoisopropylnaphthalene (MIPN) by alkylation of naphthalene using zeolites of the faujasite type, the cations of which have been replaced by alkaline earth metal ions, as catalysts.

2-Monoisopropylnaphthalene (2-MIPN) is a valuable intermediate for the preparation of 2-naphthol by the Hock process. In the case of the conventional process for the preparation of 2-naphthol, the Na salt of 2-naphthalenesulfonic acid is as a rule reacted in a baking melt to give the 2-naphtholate, from which 2-naphthol is liberated by subsequent acidification. In the case of this process a large amount of salts is obtained. This disadvantage is substantially overcome by means of the Hock process.

When naphthalene is alkylated, dialkylated and trialkylated products, and in the case of higher conversions even more highly alkylated naphthalenes, are formed in addition to the monoalkylated products. 1- and 2-MIPN are present in the monoisopropylnaphthalene fraction.

In the diisopropylnaphthalene fraction (DIPN), 2,6-diisopropylnaphthalene (2,6-DIPN) is also a valuable intermediate for many highly refined products. Thus, it is used, inter alia, as starting material for the preparation of 2,6-naphthalenedicarboxylic acid, 2,6-dihydroxynaphthalene and 6-hydroxy-2-naphthalenecarboxylic acid. These compounds are used as monomers for high performance polymers.

In practice, because of the relatively large amount of 2-naphthol produced, the demand for 2-MIPN is considerably greater than the amount of 2,6-DIPN required for the preparation of monomers. Therefore, it is desirable to direct the alkylation in such a way that a high selectivity for MIPN and, at the same time, a high proportion of 2-MIPN in the MIPN fraction, is obtained.

It is known that very diverse acid catalysts can be used for the alkylation of naphthalene to MIPN and also DIPN. When the alkylation is carried out using Friedel-Crafts catalysts, such as $AlCl_3$ or $BF_3$, salts are formed during working up and the catalyst is destroyed. In addition, resin-like compounds form in the course of the reaction and these interfere in working up. The separation of the products from the catalyst is usually laborious. The catalysts are highly corrosive and continuous processes can be achieved only with difficulty. Therefore, attempts have been made for some time to replace this type of catalysts by solid acids.

In German Patent 2 644 624, a process is described for the preparation of 2-MIPN using $H_3PO_4/SiO_2$. In this process naphthalene has to be used in a large excess in order to prevent the formation of polyalkylated products. The naphthalene conversion is limited to at most 60%. The naphthalene which is still unconverted is separated off and recycled into the alkylation. Subsequent isomerization of the reaction mixture is necessary in order to obtain a sufficiently high proportion of 2-MIPN. Naphthalene also has to be used in excess, in order to prevent the formation of large amounts of polyalkylated products, when acid-activated montmorillonite (German Offenlegungsschrift 2 208 363) or perfluorinated sulfonic acid resins (U.S. Pat. No. 4,288,646) are used. The low degree of conversion of naphthalene in all of these processes is a considerable disadvantage.

In other research the possibility for shape-selective catalysis is used in order to prepare the 2-alkyl- and 2,6-dialkylnaphthalene. Shape-selective catalysis signifies that the dimensions of the molecules or transition states participating in the reaction are of the same order of magnitude as those of the catalyst pores. The course of reaction can be influenced by steric restraints. Thus, for example, in the case of the alkylation of naphthalene with methanol using zeolites of the ZSM-5 type the slim β-isomers (2-methyl- and 2,6-dimethylnaphthalene) can be obtained with high selectivity (for example D. Fraenkel et al., J. Catal. 110 (1987) 123–132 and European Published Specification 280 055). However, in the case of these processes also the naphthalene conversion is limited because the diffusion of the bulky molecules through the zeolite pores is severely hindered.

In the process of European Published Specification 317 907, a dealuminized mordenite zeolite was used for the alkylation of naphthalene with propene. A naphthalene conversion of 97.3% was achieved. The DIPN yield was 68%, 50% of which comprised 2,6-DIPN. No information was given on the yield of MIPN and the composition of this fraction. A dealuminized mordenite zeolite is also used in the process according to WO 90/03961 for the selective preparation of 2,6-DIPN. It is stated that the proportion of 2,6-DIPN in the DIPN fraction becomes larger than the proportion in the thermodynamic equilibrium and the ratio of 2,6-/2,7-DIPN becomes greater than 1.2 as a result of this type of zeolite. Thus, for example, for 27% conversion of naphthalene, the proportion of 2,6-DIPN is said to be 70% and the ratio of 2,6-/2,7-DIPN to be 3.0 and the ratio of MIPN/(DIPN+TIPN) to be 5.1. If the conversion is raised to 78%, the proportion of 2,6-DIPN falls to 62% and the ratio of 2,6-/2,7-DIPN to 2.6 and the ratio of MIPN/(DIPN+TIPN) to 1.1. No data are given with regard to the composition of the MIPN fraction.

These examples show that mordenite catalysts severely suppress the formation of MIPN compared with DIPN with increasing conversion of naphthalene.

Faujasites have also already been used as catalysts for the alkylation of naphthalene. In U.S. Pat. No. 3,251,897 and German Patent 1 468 982, the use of Y-zeolites, which have been exchanged with rare earth metal ions and/or protons, for the alkylation of naphthalene is described. The naphthalene conversion was, however, low and the catalysts had only short lives. In German Patent 1 468 982 it is stated that $Ca^{2+}$- and $Mg^{2+}$-exchanged X- and Y-zeolites do not catalyze the alkylation of aromatic compounds, such as the ethylation of benzene, whereas the X- and Y-zeolites exchanged with rare earth metal ions are highly active for this reaction.

In EP-A 338 292 and EP-A 432 132 the reaction of naphthalene with propene on dealuminized Y-zeolites ($SiO_2/Al_2O_3$=10 to 350) in proton form in the presence of decalin and using hydrogen as carrier gas is described. At 220° C. and with a naphthalene conversion of about 50%, the selectivity in this process is between 68 and 75% for MIPN, between 24 and 30% for DIPN and between 1.5 and 3% for triisopropylnaphthalene (TIPN). The proportion of 2-MIPN in the MIPN is between 91.5 and 93.5%. No information is given on the composition of the DIPN. The alkylation of MIPN with a 2-MIPN content of 93% to DIPN is also described. The proportion of 2,6-DIPN in the DIPN fraction is about 40% in this case. A disadvantage of this process is that large amounts of the high-boiling inert diluents have to be separated off from the product mixture during working up.

The aim of the present invention was to provide a process for the preparation of MIPN by alkylation of naphthalene, which process does not have the disadvantages described above and provides as high as possible a selectivity for MIPN, coupled with a high proportion of 2-MIPN in the MIPN fraction, in particular with a high conversion of naphthalene.

This is achieved according to the invention by the use of zeolites of the faujasite type, the cations of which have been replaced by alkaline earth metal ions, as catalysts. In this process monoalkylated products containing a high proportion of 2-MIPN are formed with high selectivity.

The invention now relates to a process for the preparation of monoisopropylnaphthalene by alkylation of naphthalene with the aid of zeolites of the faujasite type as catalysts, which comprises replacing the cations of the zeolites by alkaline earth metal ions.

Zeolites are crystalline aluminosilicates. Si and Al atoms are surrounded tetrahedrally by O atoms. The tetrahedra are linked via common O atoms and form a crystal structure which is permeated by defined pores and cavities (cf. D. W. Breck, Zeolite Molecular Sieves, John Wiley & Sons, (1974), pp. 29–185).

Zeolites of the faujasite type, the cations of which have been replaced by alkaline earth metal ions, are suitable for the process according to the invention. The structure of these zeolites is characterized by cuboctahedra (sodalite units), which are linked to one another by double hexagonal rings. A cubic lattice forms, in which large cavities (supercages) are linked three dimensionally by pores. The pores are bounded by 12 Si and Al atoms and have a diameter of 0.74 nm. The supercages have a diameter of 1.3 nm. Amongst all of the zeolites, the faujasites have the most pores and cavities (D. W. Breck, loc. cit.). They therefore exert steric restraints in their interior only on very large molecules and transition states.

It is surprising that the desired high selectivity for the MIPN can be achieved with precisely this type of zeolite. The mordenite catalyst described in EP-A 317 907, which is described in many papers as a form-selective catalyst for the reaction of mononuclear aromatic compounds, such as 1-methyl-2-ethylbenzene (for example S. M. Csicsery, in Zeolite Chemistry and Catalysis, J. A. Rabo, published by ACS Monograph 171 (1976), pp. 680–713) and has pore widths of $0.65 \times 0.70$ nm (Atlas of Zeolite Structure Types, D. H. Olsen and W. M. Meier, published by Butterworths (1990)) leads to a much more extensive formation of DIPN. This also applies in the case of other zeolites, the pores of which are narrower than those of faujasites, such as beta- or EU-1-zeolites. Zeolites of the beta type have a three-dimensional pore system. The pore radii are $0.57 \times 0.75$ nm and $0.56 \times 0.65$ nm (J. B. Higgins et al., Zeolites 8 (1988), pp. 446–452). The pores of EU-1-zeolites are bounded only by 10 Si and Al atoms and have a diameter of $0.41 \times 0.57$ nm. However, the pores have large lateral bulges (Atlas of Zeolite Structure Types, D. H. Olsen and W. M. Meier, published by Butterworths (1990)). A few results of alkylation on the various zeolites are compared in the examples. Comparison experiments using lanthanum-exchanged Y-zeolites showed that the latter are active with respect to the alkylation reaction. However, by-products (in particular tetralin and isopropyltetralins as well as high-boiling compounds) were detected in large amounts in the alkylate.

The zeolites of the faujasite type used according to the invention are commercially available and can be prepared with $SiO_2/Al_2O_3$ ratios of between 2 and about 7 by known processes. The faujasites richer in aluminum are termed X-zeolites $SiO_2/Al_2O_3=2$ to 3) and those poorer in aluminum are termed Y-zeolites ($SiO_2/Al_2O_3=3$ to 7). However higher $SiO_2/Al_2O_3$ ratios can be obtained by subsequent dealumination. The aluminum content can be reduced in diverse ways. A few methods are described, for example, in J. Scherzer, Catalytic Materials; Relationship between Structure and Reactivity, ACS Symp. Ser. 248 (1984), pp. 175–200. Faujasites having $SiO_2/Al_2O_3$ ratios of between 4 and 400, preferably between 5 and 200, are particularly suitable for the process according to the invention.

In order to convert the zeolite into a catalytically active, i.e. acid, form, the $Na^+$ ions present are exchanged by ion-exchange for alkaline earth metal ions. In addition to the alkaline earth metal ions, small amounts of rare earth metal ions and/or ammonium ions or protons can also be present in the zeolite. In this context it is expedient that at least 50% of the negative lattice charges are compensated by alkaline earth metal ions. Preferably, at least 95% of the exchangeable $Na^+$ ions are replaced by alkaline earth metal ions. Suitable alkaline earth metal salts, which are used for ion exchange, are all water-soluble salts, in particular chlorides and nitrates. The zeolite is then converted into the catalytically active form by dehydration (and deammoniation in the case of $NH_4^+$ forms) at 200° to 800° C., preferably at 250° to 550° C. Suitable catalysts are, in particular, $Ca^{2+}$ and $Mg^{2+}$ ion-exchanged faujasites (i.e. X-and Y-zeolites). They are designated CaY and CaX or MgY and MgX below.

The alkylation reaction can be carried out in the gas phase, but preferably in the liquid phase. Alkylating agents which can be used are, for example, i-propanol, propene, i-propyl chloride and i-propyl bromide. In the case of the gas phase reaction it is preferable to react naphthalene with propene or i-propanol. In the case of the alkylation in the liquid phase, the use of propene is preferred.

The reaction temperature is expediently between about 100° and 500° C., preferably between about 150° and 300° C. An elevated pressure is favorable for the course of the alkylation, especially if the alkylation is carried out using propene. The reaction can be carried out under reduced pressure, atmospheric pressure or elevated pressure, for example at up to about 100 bar, preferably at between about 2 and 20 bar.

The alkylation in the liquid phase can be carried out in all suitable apparatus, most simply discontinuously in a stirred vessel using catalysts in powder form suspended in molten naphthalene. However, the process can also be carried out continuously in the liquid phase. Propene is then passed through the suspension at the reaction temperature or injected under pressure until the desired pressure is obtained. Inert gases, such as nitrogen, can also be used in order to obtain the reaction pressure.

With respect to the mass of naphthalene employed, it is particularly advantageous, in the case of the discontinuous method, to use between about 0.1 and 50% by weight of catalyst, preferably between about 1 and 10% by weight. The reaction time can be between about 0.5 h and several days, in particular between 2 and 10 h, depending on the reaction conditions and the desired conversion. After the reaction has taken place, the zeolite can be separated off from the reaction mixture in a simple manner, for example by filtration.

In principle, all apparatus suitable for gas phase reactions can be used for carrying out the reaction in the gas phase. A fixed bed flow reactor is technically the simplest to operate. In this case the catalyst can be incorporated in the reactor in the form of pellets. For preparation of the pellets, the zeolite can be compressed together with a binder such as $Al_2O_3$ or $SiO_2$, or alternatively binder-free. Suitable binders are, in particular, aluminum oxides, hydroxides or hydroxy chlorides and the silicon, titanium and zirconium oxides, as well as clay materials.

The naphthalene can be metered into the reactor in the molten state or dissolved in an inert solvent and vaporized upstream of the catalyst bed or, alternatively, already converted into the gaseous state upstream of the reactor and fed in this state into the reactor. The reaction is preferably carried out without using solvents.

i-Propanol can be metered in the same way as naphthalene. Propene is introduced in gas form. The reactants can be used on their own or as a mixture with a gas which is inert with respect to the reaction, such as hydrogen or nitrogen. However, it is preferred to carry out the reaction without inert solvents or gases. The products are condensed after leaving the reactor.

The molar ratio of naphthalene to alkylating agent is expediently in the range from about 0.1 to 10, preferably from about 0.2 to 1.2, in the case of the continuous procedures.

The dwell time of the reactants is generally between about 0.05 and 20 s, preferably between 1 and 10 s. The space velocity (LHSV=liquid hourly space velocity=ml of feed per ml of catalyst volume and per hour) can preferably be set in the range from 0.1 to 5 $h^{-1}$, the range between 0.5 and 2 $h^{-1}$ being particularly favorable.

The catalyst can be used several times for the reaction. If it has been deactivated, it can be regenerated again by calcination in an oxidizing atmosphere, preferably in air, at about 350° to 800° C., preferably at about 500° to 600° C.

The proportion of 2-MIPN in the product mixture can be further increased to, at the maximum, the equilibrium content (at 200° C. the 2-MIPN content of the MIPN fraction at equilibrium is about 95%) in a further process step by isomerization, likewise with the aid of acid faujasites as catalysts. For this reason the objective of obtaining a high proportion of 2-MIPN in the MIPN fraction is subsidiary to the objective of a high selectivity for MIPN. Within the DIPN fraction, the 2,6-DIPN content can also be increased by subsequent isomerization. At 200° C. it is about 42% at equilibrium. It is a further advantage of the process that two valuable products (2-MIPN and 2,6-DIPN) can be prepared at the same time.

The more highly alkylated naphthalenes formed during the alkylation can be converted to MIPN again by transalkylation with naphthalene. The transalkylation is a secondary reaction of isomerization and can therefore take place in the same process step as the isomerization. Alkaline earth metal-exchanged zeolites of the faujasite type are also active for the isomerization and transalkylation of isopropylnaphthalenes.

The product mixture can initially be separated by distillation into unconverted naphthalene, MIPN, DIPN and TIPN. Unconverted naphthalene can either be re-used for the alkylation or, alternatively, can be fed together with the more highly alkylated reaction products into the isomerization/transalkylation step. 2-MIPN can be separated off from the MIPN fraction by crystallization, if appropriate from a solvent such as methanol or i-propanol, or by sorption on molecular sieves (see, for example, German Offenlegungsschrift 2 517 591). The 1-MIPN-enriched filtrate can be converted into a 2-MIPN-rich mixture again by isomerization on diverse zeolites (see, for example, U.S. Pat. No. 4,026,959). 2,6-DIPN can likewise be separated off from the DIPN fraction by crystallization (see, for example, European Patent 216 009). An adsorptive separation is described, for example, in Japanese Published Specification 01 199 921. The remainder of the DIPN fraction, largely freed from 2,6-DIPN, can be converted, together with naphthalene, to MIPN again by transalkylation. 2-MIPN and 2,6-DIPN can be purified to the desired degree by subsequent conventional purification steps.

EXAMPLES

The $Na^+$ ions of the Y-zeolites used $SiO_2/Al_2O_3$ 5.4) were exchanged for the corresponding cations by ion exchange using alkaline earth metal chlorides (or rare earth nitrates in the case of Comparison Example C4). In this operation the zeolite was treated with the 10-fold amount of 10% aqueous solutions of these salts under reflux for 6 to 7 h. This exchange was repeated 3 times. In Example 1, 85% of the sodium ions were exchanged for calcium ions and in Example 2 70% of the sodium ions were exchanged for magnesium ions.

Low-aluminum Y-zeolites were prepared by dealumination with $SiCl_4$ in accordance with the method of H. Beyer, described in H. Beyer and I. Belenykaya, Stud. Surf. Sci. Catal. 5 (1980), pp. 203-210. These low-aluminum zeolites were yet further dealuminized by repeated boiling with the 10-fold amount of 1N HCl. After this treatment the zeolites were calcined at 550° C.

The comparison zeolites, which have other structures, were prepared by hydrothermal synthesis in accordance with methods from the literature. Zeolite beta was synthesized with a $SiO_2/Al_2O_3$ ratio of 23 in the gel in accordance with Example 7 of U.S. Pat. No. 3,308,069. Mordenite crystallized in a modified beta synthesis in accordance with the abovementioned method, equimolar amounts of tetraethylammonium bromide and NaOH being used in place of tetraethylammonium hydroxide. The crystallization of EU-1-zeolites is described in G. W. Dodwell et al., Zeolites 5 (1985), pp. 153-157. After crystallization, the zeolites were filtered off, dried and calcined in air at 550° C. They were then treated twice with 10% aqueous $NH_4NO_3$ solution and calcined again. Mordenite, like the Y-zeolites, was additionally treated once with 1N HCl for one hour and also calcined.

Examples 1 and 2 and Comparison Examples C1 to C4 were carried out in a stirred vessel. Before the reaction, the zeolite was dried for 1 h at 300° C. and then suspended in powder form in 128 g of molten naphthalene. 5% by weight of zeolite, with respect to naphthalene, were used. Propene was passed through the suspension under atmospheric pressure at a rate of 6.5 l/h.

The reaction temperature was 200° C. The test results are summarized in the Table.

The results of the naphthalene alkylation with the zeolites according to the invention show that high selectivities for MIPN $S_{MIPN}$ (more than 90 mol-% in the case of $X_N=20$ mol-% naphthalene conversion) can be achieved.

Compared with these, the MIPN selectivities which are achieved with Hmordenite and Hbeta (C2 and C3) are distinctly lower. It is true that HEU-1 (C1) also gives a high MIPN selectivity, but the 2-MIPN contents $C_{2\text{-}MIPN}$ in the MIPN fraction are distinctly lower than the contents achieved in Examples 1 and 2. With Hmordenite, as described in the literature, a high 2,6-DIPN content $C_{2,6\text{-}DIPN}$ is obtained; however, in addition to the low selectivity for MIPN, the conversion achieved after a test period of 6 h is also distinctly lower. Lanthanum-exchanged zeolites (C4) show a low selectivity for MIPN because of the large number of by-products.

TABLE

| Example | Zeolite | SiO$_2$/Al$_2$O$_3$ | Naphthalene conversion after 6 h, mol % | $S_{MIHN}$, mol % for $X_N$ mol % | | | $C_{2\text{-}MIHN}$, % for $X_N$ mol % | | | $S_{DIHN}$, mol % for $X_N$ mol % | $C_{2,6\text{-}DIHN}$, % for $X_N$ mol % | Yield of BP$^{a)}$ after 6 h | |
|---|---|---|---|---|---|---|---|---|---|---|---|---|---|
| | | | | 20 | 40 | 60 | 20 | 40 | 60 | 40 | 40 | T$^{b)}$, % | HB$^{c)}$, % |
| 1 | CaY | 5.4 | 86 | 92 | 85 | 77 | 83 | 89 | 90 | 14 | 30 | 0.2 | 1.0 |
| 2 | MgY | 5.4 | 68 | 94 | 88 | 82 | 68 | 70 | 63 | 14 | 20 | 0.1 | n.d.$^{d)}$ |
| C1 | HEU-1 | 49 | 67 | 94 | 85 | 74 | 62 | 60 | 59 | 14 | 18 | 0 | 0.1 |
| C2 | Hmordenite | 17 | 38 | 88 | 81 | | 81 | 76 | | 19 | 60 | 0 | <0.1 |
| C3 | Hbeta | 12 | 82 | 89 | 78 | 66 | 91 | 89 | 84 | 20 | 41 | 0 | 0.5 |
| C4 | LaY | 5.4 | 86 | 80 | 75 | 67 | 93 | 92 | 91 | 12 | 31 | 1.5 | 9 | a) BP: By-products
b) T: Tetralin and isopropyltetralins
c) HB: High-boiling by-products
d) n.d.: Not determined

We claim:

1. A process for the preparation of monoisopropylnaphthalene, comprising:
   contacting naphthalene and an alkylating agent having 3 carbon atoms with a catalyst consisting essentially of a zeolite having a faujasite structure wherein cations of said structure have been replaced by alkaline earth metal ions, and
   alkylating the naphthalene under effective alkylating conditions and obtaining monoisopropylnaphthalene as a product.

2. The process as claimed in claim 1, wherein the alkaline earth metal ions are Mg$^{2+}$ and/or Ca$^{2+}$ ions.

3. The process as claimed in claim 1, wherein the zeolite has a SiO$_2$/Al$_2$O$_3$ ratio of about 4 to 400.

4. The process as claimed in claim 1, wherein at least 95% of the exchangeable Na$^+$ ions have been replaced by alkaline earth metal ions.

5. The process as claimed in claim 1, wherein the alkylation reaction is carried out in the liquid phase.

6. The process as claimed in claim 1, wherein the alkylation reaction is carried out at temperatures of from about 100° to 500° C.

7. The process as claimed in claim 1, wherein the alkylation reaction is carried out under a pressure of up to about 100 bar.

8. The process as claimed in claim 1, wherein the alkylating agent used is i-propyl bromide, i-propyl chloride, propene or i-propanol.

9. The process as claimed in claim 1, wherein said process is continuous, and naphthalene is alkylated in a ratio of 0.1 to 10 moles of naphthalene per mole of alkylating agent.

10. The process as claimed in claim 1, wherein said process is discontinuous, and about 0.1 to 50% by weight of catalyst are used with respect to the mass of naphthalene employed in said process.

11. The process as claimed in claim 1, wherein: the zeolite has a SiO$_2$/Al$_2$O$_3$ ratio of 5 to 250, and the alkylation reaction is carried out a temperature of from about 150° to 300° C., under a pressure of 2 to 20 bar.

12. The process as claimed in claim 9, wherein said ratio is 0.2 to 1.2 moles of naphthalene per mole of alkylating agent.

13. The process as claimed in claim 10, wherein about 1 to 10% by weight of catalyst are used with respect to the mass of naphthalene employed in said process.

14. The process as claimed in claim 1, wherein said process is carried out essentially in the absence of solvent.

15. The process as claimed in claim 1, wherein the selectivity for the monoisopropylnapththalene is greater than 90 mol-% at the stage of the alkylating step at which 20 mol-% of the naphthalene has been converted.

16. The process as claimed in claim 1, comprising:
   alkylating the naphthalene with the alkylating agent in the presence of a catalyst consisting essentially of a zeolite having a faujasite structure and negative lattice charges, at least 50% of said charges being compensated for by alkaline earth metal ions.

* * * * *